US007179639B2

(12) United States Patent
Pottathil et al.

(10) Patent No.: US 7,179,639 B2
(45) Date of Patent: Feb. 20, 2007

(54) THERMAL STRIP THERMOCYCLER

(76) Inventors: Raveendran Pottathil, Accudx Inc., 9466 Black Mountain Rd., Suite 130, San Diego, CA (US) 92126; Jerome Anton Streifel, Accudx Inc., 9466 Black Mountain Rd., Suite 130, San Diego, CA (US) 92126

( * ) Notice: Subject to any disclaimer, the term of this patent is extended or adjusted under 35 U.S.C. 154(b) by 484 days.

(21) Appl. No.: 10/382,755

(22) Filed: Mar. 5, 2003

(65) Prior Publication Data

US 2004/0096958 A1 May 20, 2004

Related U.S. Application Data

(60) Provisional application No. 60/361,365, filed on Mar. 5, 2002.

(51) Int. Cl.
*C12M 1/34* (2006.01)

(52) U.S. Cl. .............................. 435/287.2; 435/303.1; 435/6; 435/286.1; 436/515; 436/516

(58) Field of Classification Search .................... None
See application file for complete search history.

(56) References Cited

U.S. PATENT DOCUMENTS

| | | | | |
|---|---|---|---|---|
| 4,683,195 | A | | 7/1987 | Mullis et al. |
| 4,683,202 | A | | 7/1987 | Mullis et al. |
| 5,038,852 | A | | 8/1991 | Johnson et al. |
| 5,176,203 | A | | 1/1993 | Larzul |
| 5,188,963 | A | * | 2/1993 | Stapleton ................. 435/288.3 |
| 5,224,778 | A | | 7/1993 | Grossman et al. |
| 5,314,809 | A | | 5/1994 | Erlich et al. |
| 5,333,675 | A | | 8/1994 | Mullis et al. |
| 5,415,839 | A | | 5/1995 | Zaun et al. |
| 5,427,911 | A | | 6/1995 | Ruano et al. |
| 5,451,500 | A | | 9/1995 | Stapleton |
| 5,455,175 | A | | 10/1995 | Wittwer et al. |
| 5,504,007 | A | | 4/1996 | Haynes |
| 5,508,197 | A | | 4/1996 | Hansen |
| 5,576,218 | A | | 11/1996 | Zurek et al. |
| 5,639,423 | A | | 6/1997 | Northrup et al. |
| 5,645,801 | A | | 7/1997 | Bouma et al. |
| 5,736,106 | A | | 4/1998 | Ishiguro et al. |
| 5,736,314 | A | | 4/1998 | Hayes et al. |
| 5,802,856 | A | | 9/1998 | Schaper et al. |
| 5,897,842 | A | | 4/1999 | Dunn et al. |
| 5,935,522 | A | | 8/1999 | Swerdlow et al. |
| 5,939,312 | A | | 8/1999 | Baier et al. |
| 5,985,651 | A | | 11/1999 | Hunicke-Smith |
| 6,004,513 | A | | 12/1999 | Albagli et al. |
| 6,013,513 | A | | 1/2000 | Reber et al. |
| 6,018,616 | A | | 1/2000 | Schaper et al. |
| 6,054,277 | A | * | 4/2000 | Furcht et al. .................. 435/6 |
| 6,132,996 | A | | 10/2000 | Hunicke-Smith |
| 6,200,781 | B1 | | 3/2001 | Tal et al. |

(Continued)

*Primary Examiner*—William H. Beisner
*Assistant Examiner*—Nathan Bowers
(74) *Attorney, Agent, or Firm*—Mridula Pottathil

(57) ABSTRACT

This is a self-contained disposable thermal cycler device in which target sequence is amplified as the samples passes over a grid of alternating temperature and then at the completion of the reaction, the amplified material is captured by probes complementary to the targeted sequence. Since the device can be sealed and is disposable, it reduces the occurrence of cross contamination or specimen carry-over.

23 Claims, 2 Drawing Sheets

U.S. PATENT DOCUMENTS

| | | | | |
|---|---|---|---|---|
| 6,203,683 | B1 | 3/2001 | Austin et al. | |
| 6,180,372 | B1 | 10/2001 | Franzen | |
| 6,413,766 | B2 | 7/2002 | Landers et al. | |
| 6,432,695 | B1 | 8/2002 | Zou et al. | |
| 6,680,193 | B1 * | 1/2004 | Fouillet et al. | 435/287.2 |
| 2001/0036634 | A1 * | 11/2001 | Chow et al. | 435/6 |
| 2002/0028456 | A1 * | 3/2002 | Mansky et al. | 435/6 |
| 2002/0122747 | A1 * | 9/2002 | Zhao et al. | 422/99 |
| 2004/0089548 | A1 * | 5/2004 | Mehta et al. | 204/450 |
| 2005/0019902 | A1 * | 1/2005 | Mathies et al. | 435/287.2 |
| 2005/0202504 | A1 * | 9/2005 | Anderson et al. | 435/6 |

* cited by examiner

THERMAL STRIP THERMOCYCLER

CROSS REFERENCE TO RELATED APPLICATION

This application claims priority from U.S. Provisional Patent Application No. 60/361,365, filed Mar. 5, 2002.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The invention relates generally to the field of nucleic amplification reactions and more particularly to a device that rapidly and economically amplifies, detects and measures polynucleotide products from nucleic acid amplification processes, such as polymerase chain reaction.

Nucleic acid sequence analysis using polymerase chain reaction (PCR) and other nucleic acid amplification techniques has been in the forefront of the rapid expansion of molecular testing and research worldwide. The development of several nucleic acid amplification technologies has played a major role in this rapid expansion of nucleic acid analysis. A variety of instrumentation has been developed to perform nucleic acid analysis, the most widespread being PCR technology.

The polymerase chain reaction (PCR), as described in U.S. Pat. Nos. 4,683,195 and 4,683,202 to Mullis and Mullis et al., describe the basics of what has become PCR technology for increasing the concentration of a segment of target sequence in a mixture of genomic DNA without cloning or purification.

PCR technology or methodology has become the de facto standard for the amplification of nucleic acid. The most ubiquitous nucleic acid amplification systems that have been developed to perform PCR and other nucleic amplification techniques are comprised of thermal cycler instruments that have as their major component a thermal conductive block of material that alternately heats and cools a thermal conductive container, usually made of glass or plastic, placed on it. This container holds a fluid sample mixture containing the targeted genetic specimen material and reagents (in the case of a PCR amplification the fluid sample contains nucleic acid material, thermostable DNA polymerase and primers designed with sequences complementary to the targeted nucleic acid). The primers may contain at the 5' end may contain a convenient reporter molecule such as radioisotope, biotin, floriscein, etc. During a PCR reaction, the thermal cycler instrument alternately heats and cools the thermal conductive block on which the sample material is in contact; cycling the sample mixtures first to a temperature of approximately 95° C., causing the denaturation of the double-stranded then cooling it to a temperature approximately 55° C. allowing the primers in the sample mixture to anneal to the resulting single-stranded templates from the specimen and then heating the sample mixture to approximately 72° C. where the thermostable DNA polymerase synthesizes a new strand of DNA from the extension of the primer annealed to the template complementary to that of the single-stranded DNA template creating 2 new double-stranded DNA pairs. The thermal cycler then continues to cycle the sample mixture through the 95° C. to 55° C. to 72° temperatures replicating the denaturation, annealing and synthesis processes and doubling at each cycle the targeted DNA before it is fully amplified resulting in the amplification of the original genetic material or DNA fragment to over $10^9$ its original number. The amplified material is then removed from the thermal cycler placed in an instrument or on a device containing a probe complementary to the targeted material that will fluoresce in proportion to the amount of targeted material in the amplified sample.

Newer models of thermal cycler instruments have built-in detection apparatus that automatically detect the presence of the targeted genetic material once it is amplified.

Critical to the successful PCR amplification of sample material is the heating and cooling of the sample to the required temperatures, the presence of a sufficient amount of thermostable DNA polymerase needed to synthesize new DNA strands plus a large excess of primers, so that the two strands will always bind to the primers, instead of with each other, and a reaction that is carried out in a closed or sealed reaction environment that prevents cross contamination or sample carryover. Without these conditions being met it is highly unlikely that the thermal cycle amplification process will be successful.

Recent advances in thermal cycler technology have resulted in air-based temperature control using hot air jets to rapidly heat and cool the sample material or heating and cooling the sample materials in microfluidic chambers, thereby replacing the thermal conductive block system. Some of these newer technologies continuously or at various times during the amplification detect or identify the targeted amplified genetic material.

These advances in prior art thermal cycler technology have not alleviated all of the problems with the prior art. There still exists a need to improve prior art that while significantly reducing the time required to amplify nucleic acid material down to thirty (30) minutes still require highly trained technicians to operate, are largely fixed immobile instruments that weigh from 12 to 25 kilograms, remain subject to cross contamination and sample carryover and result in a significant increase in the thermal cycler system cost of ownership and an increase in the reagent cost per analysis.

One skilled in the art will readily appreciate that the present invention is well adapted to carry out the objectives and obtain the ends and advantages mentioned as well as those inherent therein and represents a significant advancement over prior art.

BRIEF SUMMARY OF THE INVENTION

It is the general object of this present invention to provide a miniaturized thermal cycler capable of solving the above stated problems with prior art. It is the specific objective of this invention to provide an inexpensive, easy to use, easily transported thermal cycler, which provides for a more rapid thermal cycling and capture of amplified biochemical or molecular biological reactions and in particular a more rapid method for amplification, capture and detection or measurement of target sequence nucleic acid in a polymerase chain reaction within a closed disposable device that eliminates cross contamination or sample carryover.

The invention is based on the use of printed or electronic circuit technology as the method of forming the thermal cycler heating elements and in certain embodiments the cooling elements, and is based on the flow of fluids in thin membranes or films in order to provide a more economical manufactured and disposable device that amplifies target sequences much more rapidly than existing thermal cycler technology.

In certain embodiments, it is also based on the inclusion of some of the reagents necessary for extraction and reaction being included in the sample addition pad and/or porous membrane. This conserves expensive reagents by supplying them only as needed to the leading edge of the reaction.

The temperature cycling of the fluid sample is more rapid because the reactions taking place in the fluid sample material take place within the thin layer of the membrane and in close contact with the heating element.

The device consumes less power compared to the state of the art because of its miniaturization of the heating and cooling elements unlike the state of the art which expends a much larger amount of power in order to alternately heat and cool the thermal blocks or air temperature controllers and the thermal conductive container in which the fluid sample is held. In addition, the reduced power and miniaturization lends the device to be easily adaptable to mobile use.

The invention is adaptable to include options including temperature sensing using applied voltages for temperature control.

DETAILED DESCRIPTION OF THE INVENTION

Figure 1:
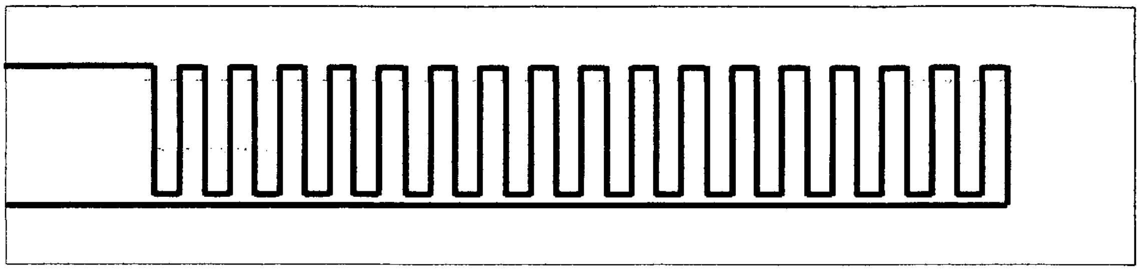
FIG. 1 Version 1—Resistive conductor is printed on the support matrix in a sinuous pattern. A voltage is applied across the ends of the conductors. The temperature is determined by the current, which is dependent on the applied voltage, and on the heat transfer of the support matrix.
Figure 2:
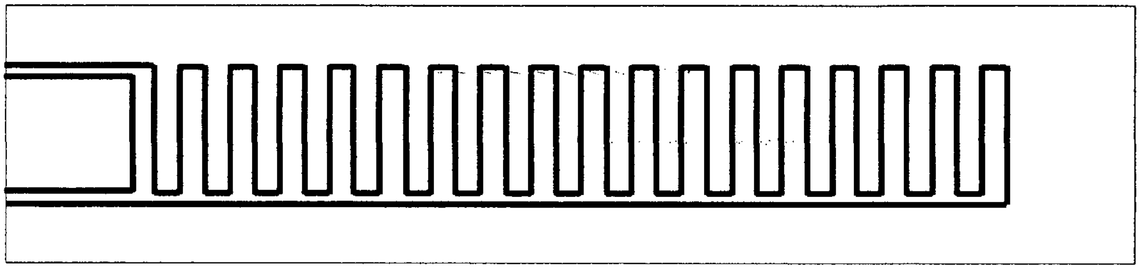
FIG. 2 Version 2—The same as version 1 except with a second circuit on one end to provide a higher temperature for the initial cycle.
Figure 3:
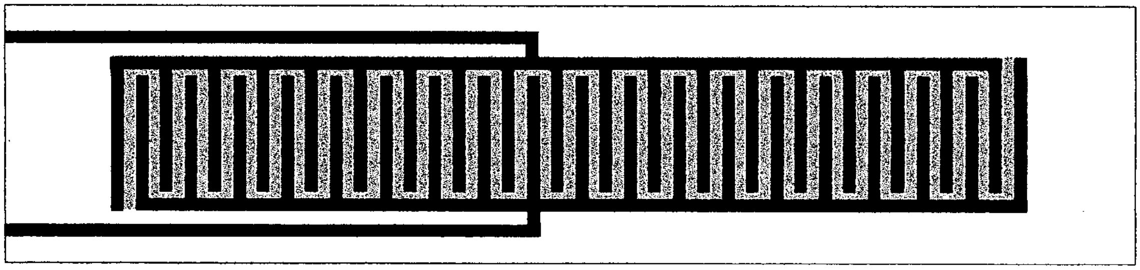
FIG. 3. Version 3—Two low resistant conductors are printed in an intermeshing comb patterns on top of a resistive conductor. Voltage is applied across the two halves of the pattern. Current flows across the resistive layer generating heat.
Figure 4:
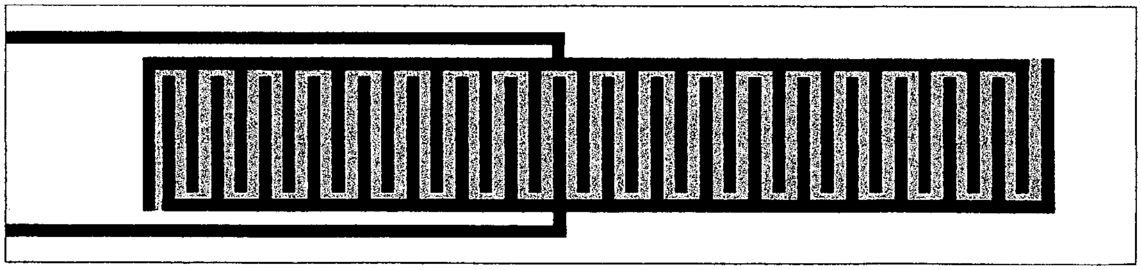
FIG. 4. Version 4—The same as version 3 except with a closer spacing of the first comb teeth to provide less resistance and a higher temperature for the initial cycle.
Figure 5:
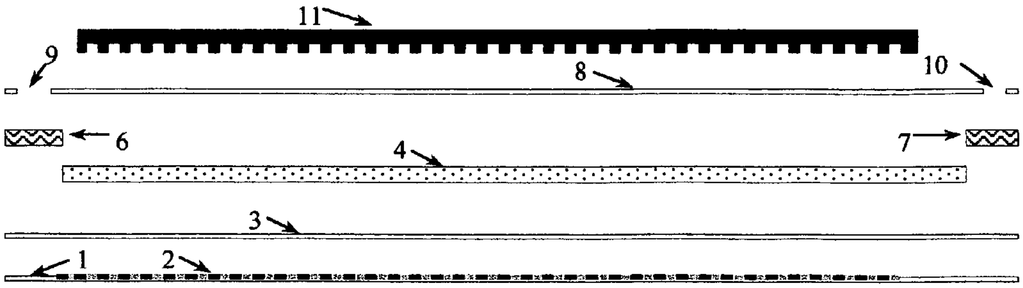
FIG. 5. Exploded cross sectional view of the components with Version 3 of the thermal strip. Support matrix (1) of the printed circuit (2). Impermeable membrane (3). Porous membrane (4). Sample addition pad (6). Fluid absorption pad (7). Impermeable membrane (8) with sample addition opening (9) and vent hole (10). Heat sink with contact ridges (11).
Figure 6:
FIG. 6. Assembled cross sectional view of components shown in FIG. 5.
Figure 7:
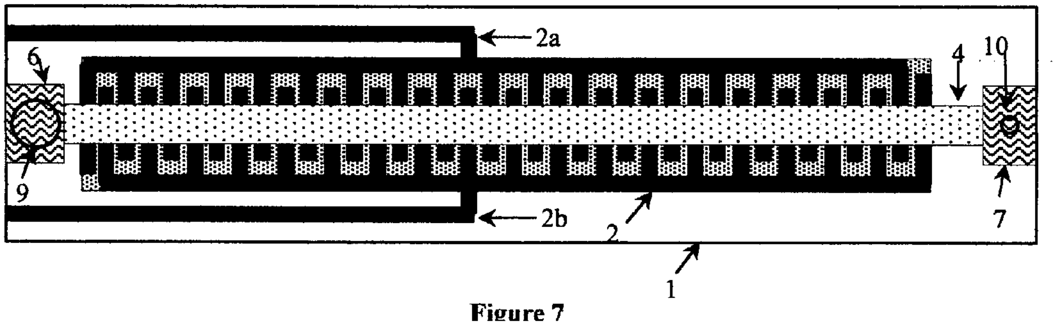
FIG. 7. Top view of assembled components shown in FIG. 6 but without the heat sink.
Figure 8:
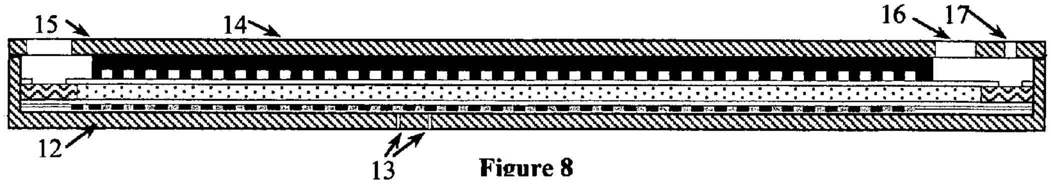
FIG. 8. Cross sectional view of the components contained in a case comprising a case bottom (12) with access holes for temperature monitoring (13), and case top (14) with sample addition hole (15), capture zone viewing port (16) and vent hole (17).

The invention is a rapid thermal cycler device with reagent-impregnated media directly affixed to it that amplifies and captures the product of biochemical or molecular biological reactions.

The functional part of the device consists of a support material upon which the conductive circuits are applied, herein referred to as the thermal strip. The circuits can generate heat by either resistive current flowing along a conductor or by electrical current flow between two conductors across a resistive layer. An impermeable membrane layer covers the thermal strip. The thermal strip is easily produced by an inexpensive printing process and is easily adaptable to various configurations to include heating with multiple circuits and with resistive flow along the conductor or across a resistive layer between two conductors. Variations in the thermal strip heater design are shown in FIGS. 1–4. The device is shown in FIGS. 5–8.

A porous rectangular membrane is affixed to the impermeable membrane layer covering the thermal strip. The porous membrane can be comprised of a backed or non-backed porous membrane material with or without an impermeable membrane affixed to the side of the porous membrane opposite the side in closest proximity to the thermal strip.

On the proximal end of the porous membrane, there is a sample addition pad affixed on top of the porous membrane, and on the distal end of the porous membrane, there is a fluid absorption pad affixed on top of the porous membrane.

Reagents may be contained in the membrane such that during the flow of the fluid sample vital components of the reaction mixture that are consumed or lost due to inactivation or differential flow are replenished.

The thermal strip, porous membrane, sample addition pad and fluid absorption pad are enclosed in a sealed impermeable case to prevent fluid sample solution evaporation, except for openings at the sample addition pad and a vent at the fluid absorption pad at the distal end of the membrane. The enclosed thermal strip porous membrane device is disposable.

The fluid sample is introduced to the device at the sample addition pad and flows through the porous membrane material during the thermal cycling process until the amplification is complete and the amplified sample material is captured by a probe complementary to the targeted sequence applied at the distal end of the porous membrane.

The device will be read in an instrument, which can detect signal generated by a variety of reporter groups, such as fluorescence, color, bioluminescence, chemiluminescence, etc. Such an instrument might also house the power source for the thermal cycler strip and can be easily and inexpensively manufactured or licensed from a commercial source.

Completion of the assay can be indicated by a similar arrangement of electrodes at the fluid absorption pad or by inclusion of a dye on part of the fluid absorption pad that is not visible and that then migrates to the vent hole at the end of the strip.

In an alternative embodiment, the fluid sample may flow through capillary channels in lieu of a porous membrane. The capillary channels can be printed onto the thermal strip or can consist of channels molded in the material of the upper case which encloses the thermal strip.

Some of the reagents used to extract nucleic material from the specimen before the sample is added to the device can be immobilized in the sample addition pad to provide for reduction of the steps necessary for sample processing and amplification of the sample material.

Reagents needed for sample treatment and or for a reaction to proceed can be placed in the sample addition pad in immobilized dried in situ format or added at the time of sample addition. The sample pad may be heated by a separate heating circuit and/or may have a closeable gap separating the sample addition pad from the membrane such that sample can be incubated at a given temperature before flow into the membrane is initiated. In this embodiment, the flow can be initiated by sliding the sample addition pad and membrane either manually of by action of an instrument.

There can be several viewing ports along the length of the case enclosing the thermal strip and membrane assembly to enable monitoring of the amplification via pico green fluorescence, etc. The case can have openings or contacts for thermocouples to monitor the temperature and provide for feedback control of the applied currents.

The thermal strip can also be affixed to a heat sink layer (e.g. copper, aluminum or other heat conductive material) on either the strips lower or upper surface. This will allow for longer run times by helping to maintain the required temperature profiles.

The device can have a built in battery and control circuitry or have these functions provided externally or a combination of both. The device can consist of all parts aforementioned except for the case parts and heat sink. In this embodiment, the thermal strip, membrane, and sample addition and liquid absorption pads enclosed in a clear impermeable membrane cover are inserted into an instrument that may provide the heat sink.

A sample can be biological or environmental material including blood or water, a wipe test pad, or a filter pad from an air sampler. The sample can be processed before application to the device or added directly to the sample addition pad, which would then contain reagents necessary for sample processing.

The reagents in solution can alternatively be added after application of the sample.

For air or aerosol samples, the collection membrane can be part of or be the sample addition pad. The device would be inserted into the air collection apparatus, removed after air sampling and then a buffer solution would be added to start the assay. For air or aerosol samples, the device could also be inserted into an air collection apparatus where the air samples are collected and inserted directly into sample processing reagent solution and then directly onto the sample addition pad.

A separate heating circuit may heat the sample pad. The device can have electrodes in contact with the sample addition pad to provide control of the applied voltages so that heating does not begin until sample is added.

After the sample is applied to the sample addition pad and processed it migrates into the porous membrane and continues to flow across the heating elements of the thermal strips. The fluid is subjected to an initial high temperature, if provided for in the circuitry, and then to a series of fluctuations between two temperatures as it continues to migrate along the membrane.

When used for polymerase chain reaction amplification of DNA, a compound such as pico green can be included in the reagents. This compound detects the amount of duplex DNA produced by the amplification reaction and thus, can allow for a quantitative assay.

Figure 9:
FIG. 9. Porous membrane with detection array on the distal end. Spots are zones of different probes used for capture of DNA of different sequences. The number and arrangement of spots can be varied. The capture zones can also be in the form of a line.

The distal region of the strip can have zones of detection for various amplified products with which array detection allows for simultaneous determination of the presence of multiple targets. An example of this is shown in FIG. 9. The array format also allows for incorporation of an internal standard. The detection zone can also have a separate circuit for optimization of the temperature of the capture process. Hybridization can be visualized by detection of 5' end labeled primers using labels of fluorescein, biotin etc.

For increased sensitivity the distal end of the membrane can taper down to concentrate the flow over the capture points.

It will be readily apparent to one skilled in the art that varying substitutions and modifications may be made to the invention disclosed herein without departing from the scope and spirit of the invention.

From the detailed description of the invention herein it can been seen that the invention addresses several problems associated with prior art: The invention makes nucleic acid amplification and capture using accepted amplification technologies that, heretofore was an expensive, very complex, multiple step and lengthy process, inexpensive and easy to perform. The invention is uncomplicated and self-contained and therefore does not require trained technicians, expensive and complex instruments or special laboratory facilities to perform as required by prior art. The invention reduces the amount of expensive reagents by providing the reagents at the point of the reaction significantly reducing the cost associated with prior art. The process enabled by the invention occurs within an enclosed disposable device protecting it from cross contamination or specimen carryover, which is a major problem experienced with prior art. The invention makes nucleic acid amplification and capture a methodology that can be inexpensively performed outside of the laboratory at the point of care in physicians offices or hospitals, in the field at the site of possible biological or environmental contamination, on an R&D lab bench and for many other applications that were heretofore unable to be addressed because of the cost and complexity associated with prior art.

The following describes a prototype of one thermal strip embodiment and data derived from experiments conducted showing the successful amplification of target sequence material using the basic elements of the invention as described herein:

Example of a Thermal Strip Device

The following commercially available components were used in the assembly of the device:

1. Strip backing consisting of fiberglass Protoboard-800, Jamesco Electronics, Belmont, Calif.
2. Electrical heating elements (Advanced Micro Devices Incorporated, Ambala, India)
3. Mylar backed and topped nitrocellulose membranes (AMDI)
4. Copper sheets
5. Polyester pads
6. Absorbent pads
7. PCR master mix components [Roche Molecular Systems Inc, USA]
8. Mycobacteria tuberculum specific primer sets with 5' biotin label, myc-1 and myc-2 as well as nucleotide capture probe, myc-3 [Synthetic Genetics Inc, San Diego, USA]

Fiberglass sheets with 2 mm spaced holes were used to prepare heating element circuits. A rectangular bio-membrane (10 mm wide, 600 mm long and ×0.05 mm thick) with 100 micron thick plastic covering was applied to the board on the circuit. A sample pad 20 mm×10 mm×2 mm was applied to the anterior end of the membrane and an absorbent paper pad of the same size at the distal end to create a continuous flow capillary system through the membrane.

Terminals of the thermal/electrical circuit were connected to a Direct Current of 8 volts and 1 ampere. A number of thermisters were placed at various points, both dorsal and ventral surfaces of the membrane. Thus temperature readings closely representing the fluid temperature in the biomembrane can be determined in real time.

A heat sink was prepared as follows: A thick copper plate of 800mm×800 mm×15 mm was cut with protruding 10 equally spaced contacts that can be placed above the membrane. A "cold pack" pre-cooled at −40° C. was placed on the copper block allowing the temperature of the copper black as well as the protruding connectors well below 4° C.

Preliminary experiments has shown that once the current is applied, the heating elements bring the temperature of the membrane above the heating elements to 98° C. and the temperature of the membrane just below the heat sink connectors to be 45° C. This profile was found to be maintained at least for 60 minutes under conditions where the membrane is wet with fluid or fluid continuously flowing through the capillaries.

EXAMPLE #1

The ability of thermal strip based device to amplify known nucleotide was tested as follows:

A synthetic polymer of 99 nucleotides was synthesized with known leader sequence of 28 nucleotides [SK38] followed by 43 random sequences and 28 known sequences [complimentary SK38]. These aptamers should have a Tennis racket structure due to complete complementary sequences at two ends.

48 μl of a master mix was made as described above and was placed into a PCR tube. 2 μl of sample or control DNA was added to each PCR reaction.

The tubes were placed in the thermocycler and run in the cycling conditions given below:

94° C. for 2 minutes 35 cycles of:

94° C. for 30 seconds

56° C. for 30 seconds

72° C. for 30 seconds

Amplified material is stored at 4° C. The PCR product was viewed by conducting electrophoresis using a 3% agarose gel in Tris, Borate EDTA Buffer (TBE) buffer. Specifically, 11 grams of Tris Base, 5.7 g of Boric Acid, and 4 ml 0.5 M EDTA (pH 8.0) were added to make a final volume of 100 ml. In order to make the 3% agarose gel, the following was utilized. Five ml of 10X TBE buffer, 1.5 grams of Agarose, and 45 ml of water were placed in a flask and warmed in a microwave. Every ten seconds, the flask was carefully swirled in order to reduce air bubbles and speed the dissolving process. Next, the dissolved 50 ml of 3% agarose was placed in a cast and set using a comb in order to create the wells. Amplified DNA from various initial target concentrations were placed on the wells. The gels were run for one hour and the amplified DNA visualized by ethdium bromide staining of the double stranded DNA.

Efficacy of Thermal Strip PCR was evaluated by applying various initial target numbers ranging from 10,000 to 1000,000 in 200 ul of PCR master mix and allowing migration

```
5' ATA ATC GAG CTA TCC GAG TAG GAG AAA TNN NNN NNN NNN NNN NNN NNN NNN

3' TAT TAG GTG GAT AGG GTC ATC CTC TTT ANN NNN NNN NNN MNN NNN NNN NNN
```

Initially, serial dilutions of the micro molar aptamer library were performed in order to determine the sensitivity of the PCR reaction. PCR was performed utilizing 2 micro liters of the solutions theoretically containing 1, 10, 100, and 1,000 DNA molecules, respectively. These concentrations were used because if one could view 1 molecule after conducting PCR then the PCR would be sensitive enough to be used in this project. (One molecule may be bound to gp120 after the screening procedure and it would be necessary that it can be amplified and viewed). The PCR product was viewed utilizing ethidium bromide staining in 3% agarose.

All PCR amplification of the DNA for this project was done in 50 micro liter volumes. The components of the reaction are shown below.

The following components were added for each reaction:

| PCR reagent | Amount | Final Concentration |
|---|---|---|
| Water | 35.5 μl | — |
| 10X PCR buffer | 5 μl | 1X |
| 25 mM $MgCl_2$ | 5 μl | 2.5 mM |
| Primer Mix | 2 μl | 20 μM |
| 2.5 mM dNTPs | 1 μl | 50 μM |
| Taq Polymerase | 0.5 μl | 2.5 μM |

A master mix using the above reagent amounts was prepared. The above amounts were multiplied by the number of PCR reactions to be run.

through thermal zones of 95° C.–55° C.–72° C.–95° C. for 10 cycles. Absorbent pad containing amplified DNA was eluted, reconstituted in 50 μl of water and electrophoretically separated and visualized by ethedium bromide under UV transilluminator.

Controls were run where the no electricity was applied during migration of sample through the biomembrane.

A clearly visible DNA band corresponding to 100 base pair marker was visible only in the case where the thermal zones were established by the application of voltages showed no visible bands.

EXAMPLE #2

Amplification of Mycobacterium TB DNA from clinical samples Sputum from known TB infected individuals were collected, clarified with "sputum lysin" [Qualpro Diagnostics, Goa, India] and DNA extracted by heating in 200 ul extraction buffer containing 0.1 IN NaOH, 1% Triton X 100 and 0.1 M tris at 60° C. for 60 minutes and neutralized with 0.05 N HCl.

The DNA was added to 200 ul PCR master mix containing mycobacteria specific primers, taq polymerase, PCR buffer and magnesium. Known amounts of purified MTB DNA standards were also run in parallel. Aliquot of 100 ul were amplified using a conventional thermal cycler for 10, 20 and 30 cycles of 95° C.–55° C.–72° C. 100 ul of PCR master mix containing test DNA was applied to the sample port of Thermal Strip Thermal Cycler 3 minutes after the application of current. 200 ul of a chase buffer containing PCR buffer without Taq and dNTPs were applied after 5 minutes to recover completely the amplified DNA into the absorbent pad.

Detection of the amplified DNA: Amplified DNA was detected and quantitated by Hybrid Capture Colorimetric assay Preparation of Solid-phase:

96 well microtiter plates were coated with MTB oligo-capture probes at 100 nano-grams/well in 1 M ammonium acetate for 16 hours at 37° C. Washed wells were blocked with 1% Bovine serum albumin in Phosphate buffered saline for two hours.

Hybridization:

10 ul aliquot of Amplified DNA from conventional and Thermal strip thermal cyclers were placed in each well and 5 ul of 1 N NaOH was added to denature the DNA. 100 ul of a hybridization solution containing 2 M sodium thiocyanate and 1 M phosphate was added and incubated for 1 hour at 37° C. The wells were washed three times with PBS-tween-20, pH 7.5. 100 ul of Streptavidin-HRP (Pierce, USA) diluted 1:7000 in 1% BSA in 0.1 M tris was added and incubated for 30 minutes at 37° C. The wells were washed 5 times with PBS Tween and 100 ul of TMB (FX, San Diego, USA) and incubated in dark at room temperature for 15 minutes. The reaction was stopped by the addition of 100 ul of 1N HCl and optical density read at 450 nM.

The test has been shown to have a sensitivity of $10^6$ copy/well allowing the detection of biotin labeled products from our experimental conditions as shown in Table 1.

TABLE 1

| Target | Number of Cycles | Optical Density Conventional | Optical Density Thermal Strip |
|---|---|---|---|
| MTB 10 | 30 | 3.200 | Not done |
| MTB 10000 | 10 | 0.650 | 0.436 |
| MTB 100000 | 10 | 1.261 | 0.962 |
| MTB 100000 | 0* | 0.060 | 0.075 |

We claim:

1. A thermal strip thermocycler comprising:

a substrate, a rectangular porous membrane, overlaying the substrate and enclosed by a clear impermeable non-electrically conductive material and having a first end and a second end opposing the first end, a conductive circuit printed on a surface of the substrate, the conductive circuit having parallel alternating zones of temperature produced by resistive heating elements positioned along the conductive circuit, and positioned such that a long axis and direction of flow within the porous membrane is perpendicular to the parallel alternating zones of temperature created by the conductive circuit, a sample addition pad on the first end of and in contact with the porous membrane, a fluid absorption pad on the opposing second end of and in contact with the porous membrane, and a heat sink placed on a side of the porous membrane opposing the conductive circuit.

2. A thermal strip thermocycler according to claim 1 wherein: the porous membrane has reagents necessary for an enzymatic or chemical reaction dried onto it.

3. A thermal strip thermocycler according to claim 1 wherein: the sample addition pad has reagents necessary for an enzymatic or chemical reaction dried onto it.

4. A thermal strip thermocycler according to claim 1 wherein: the heat sink comprises a cooling bar.

5. A thermal strip thermocycler according to claim 1 wherein: the heat sink has ridges, and wherein contact of the ridges with the at least one of the substrate and the non-electrically conductive material creates an intercalating pattern relative to the conductive circuit.

6. A thermal strip thermocycler according to claim 1 wherein: the heat sink has an access for attachment of temperature sensing devices for measuring the temperature at various areas of the porous membrane.

7. A thermal strip thermocycler according to claim 1 wherein: the thermal strip thermocycler is enclosed in a case and wherein the case comprises a top face with openings for sample addition over the sample addition pad, a vent hole proximate the fluid absorption pad, a thermocouple contact for thermally monitoring a reaction, and a transparent viewing port for optically monitoring an amplification reaction.

8. A thermal strip thermocycler according to claim 1 wherein: the thermal strip thermocycler is enclosed in a case made of a clear material for optically monitoring an amplification reaction therethrough.

9. A thermal strip thermocycler according to claim 1 wherein: the conductive circuit comprises first and second conductive circuits for providing a desired temperature in an initial cycle of thermocycling.

10. A thermal strip thermocycler according to claim 1 wherein: adjacent segments of the conductive circuit have varying width dimensions.

11. A thermal strip thermocycler according to claim 10 wherein: an initial segment of the conductive circuit is narrower than adjacent segments of a sinuous pattern thereof to provide a higher temperature for an initial cycle of thermocycling.

12. A thermal strip thermocycler according to claim 1 wherein: the conductive circuit includes at least two resistive circuits powered by different voltage sources and printed in an interlacing sinuous pattern allowing for additional temperature control.

13. A thermal strip thermocycler according to claim 12 further comprising: an additional circuit to provide a higher temperature for an initial cycle of thermocycling.

14. A thermal strip thermocycler according to claim 1 wherein: the substrate comprises at least two low resistance circuits printed in an intermeshing comb pattern on a surface thereof.

15. A thermal strip thermocycler according to claim 14 further comprising: a closer spacing for a first tine of the intermeshing comb pattern of the at least two low resistance circuits to provide less electrical resistance and a higher temperature for an initial cycle of thermocycling.

16. A thermal strip thermocycler according to claim 1 wherein: said the sample pad is heated by a separate conductive circuit with a separate voltage source.

17. A thermal strip thermocycler according to claim 1 wherein: a closeable gap separates the sample addition pad from the porous membrane such that sample can be incubated at a given time before flow of sample and reagents onto the porous membrane is initiated and flow can be initiated by sliding the sample addition pad and membrane either manually or by action of an instrument.

18. A thermal strip thermocycler comprising: a substrate, a rectangular porous membrane, overlaying the substrate and enclosed by a clear impermeable non-electrically conductive material and having a first end and a second end opposing the first end, a conductive circuit printed on a surface of the substrate, the conductive circuit having parallel alternating zones of temperature produced by resistive heating elements positioned along the conductive circuit, and positioned such that a long axis and direction of flow within the porous membrane is perpendicular to the parallel alternating zones of temperature created by the conductive circuit, wherein adjacent segments of the conductive circuit have varying width dimensions, and wherein an initial segment of the conductive circuit is narrower than adjacent segments of a sinuous pattern thereof to provide a higher temperature for an initial cycle of thermocycling, a sample addition pad on the first end of and in contact with the porous membrane, and a fluid absorption pad on the second opposing end of and in contact with the porous membrane.

19. A thermal strip thermocycler comprising:

a substrate, a rectangular porous membrane, overlaying the substrate and enclosed by a clear impermeable non-electrically conductive material and having a first end and a second end opposing the first end, a conductive circuit printed on a surface of the substrate, the conductive circuit having parallel alternating zones of temperature produced by resistive heating elements positioned along the conductive circuit, and positioned such that a long axis and direction of flow within the porous membrane is perpendicular to the parallel alternating zones of temperature created by the conductive circuit, wherein the conductive circuit includes at least two resistive circuits powered by different voltage sources and printed in an interlacing sinuous pattern allowing for additional temperature control, a sample addition pad on the first end of and in contact with the porous membrane, and a fluid absorption pad on the opposing second end of and in contact with the porous membrane.

20. A thermal strip thermocycler according to claim 19 further comprising: an additional circuit to provide a higher temperature for an initial cycle of thermocycling.

21. A thermal strip thermocycler comprising:

a substrate comprising at least two low resistance conductive circuits printed in an intermeshing comb pattern on a surface thereof, a rectangular porous membrane, overlaying the substrate and enclosed by a clear impermeable non-electrically conductive material and having a first end and a second end opposing the first end, the conductive circuits having parallel alternating zones of temperature produced by resistive heating elements positioned along the conductive circuits and positioned such that a long axis and direction of flow within the porous membrane is perpendicular to the parallel alternating zones of temperature created by the conductive circuit, a sample addition pad on the first end of and in contact with the porous membrane, and a fluid absorption pad on the opposing second end of and in contact with the porous membrane.

22. A thermal strip thermocycler comprising:

a substrate comprising at least two low resistance circuits printed in an intermeshing comb pattern on a surface thereof with a closer spacing for a first tine of the intermeshing comb pattern of the at least two low resistance circuits to provide less electrical resistance and a higher temperature for an initial cycle of thermocycling, a rectangular porous membrane, overlaying the substrate and enclosed by a clear impermeable non-electrically conductive material and having a first end and a second end opposing the first end, the conductive circuits having parallel alternating zones of temperature produced by resistive heating elements positioned along the conductive circuits and positioned such that a long axis and direction of flow within the porous membrane is perpendicular to the parallel alternating zones of temperature created by the conductive circuit, a sample addition pad on the first end of and in contact with the porous membrane, and a fluid absorption pad on the opposing second end of and in contact with the porous membrane.

23. A thermal strip thermocycler comprising:

a substrate, a rectangular porous membrane, overlaying the substrate and enclosed by a clear impermeable non-electrically conductive material and having a first end and a second end opposing the first end, a conductive circuit printed on a surface of the substrate, the conductive circuit having parallel alternating zones of temperature produced by resistive heating elements positioned along the conductive circuit, and positioned such that a long axis and direction of flow within the porous membrane is perpendicular to the parallel alternating zones of temperature created by the conductive circuit, a sample addition pad on the first end of and in contact with the porous membrane, wherein a closeable gap separates the sample addition pad from the rectangular porous membrane such that sample can be incubated at a given time before flow of sample and reagents onto the porous membrane is initiated and flow can be initiated by sliding the sample addition pad and membrane either manually or by action of an instrument, and a fluid absorption pad on the opposing second end of and in contact with the porous membrane.

* * * * *